United States Patent [19]

Ford et al.

[11] Patent Number: 5,607,707
[45] Date of Patent: Mar. 4, 1997

[54] COMPOSITIONS

[75] Inventors: Michael A. Ford, Coleford, England; Clive Mellor, Monmouth, Wales; Jayne L. Wakefield, Cinderford, England

[73] Assignee: SmithKline Beecham p.l.c., Brentford, England

[21] Appl. No.: 403,738

[22] PCT Filed: Sep. 13, 1993

[86] PCT No.: PCT/GB93/01937

§ 371 Date: Mar. 15, 1995

§ 102(e) Date: Mar. 15, 1995

[87] PCT Pub. No.: WO94/06310

PCT Pub. Date: Mar. 31, 1994

[30] Foreign Application Priority Data

Sep. 15, 1992 [GB] United Kingdom ............... 9219524

[51] Int. Cl.$^6$ ............... A23L 1/275; A23L 2/42; A23D 7/06; A23B 4/14
[52] U.S. Cl. ............... 426/2; 426/602; 426/262; 426/604; 426/540; 426/541; 426/73
[58] Field of Search ............... 426/2, 602, 262, 426/604, 540, 73

[56] References Cited

U.S. PATENT DOCUMENTS

| | | |
|---|---|---|
| 3,886,294 | 5/1975 | Emodi . |
| 3,998,753 | 12/1976 | Antoshkiw et al. . |
| 4,435,427 | 3/1984 | Hoppe et al. . |
| 4,504,499 | 3/1985 | Finnan ................... 426/250 |
| 5,023,095 | 6/1991 | Kirk . |
| 5,185,719 | 2/1993 | Dhong et al. . |
| 5,290,605 | 3/1994 | Shapira . |

FOREIGN PATENT DOCUMENTS

| | | |
|---|---|---|
| 2281961 | 8/1975 | France . |
| 4020874 | 1/1991 | Germany . |
| 1407779 | 9/1975 | United Kingdom . |
| 2012547 | 8/1979 | United Kingdom . |
| 2190822 | 12/1987 | United Kingdom . |
| 2254771 | 10/1992 | United Kingdom . |

*Primary Examiner*—Esther Kepplinger
*Assistant Examiner*—Choon P. Koh
*Attorney, Agent, or Firm*—William T. King; Edward T. Lentz

[57] ABSTRACT

An aqueous composition for the preparation of optically clear products for use in human or animal healthcare comprising 0.1 to 2.0% w/w of an oil-soluble ingredient as a 20–30% w/w dispersion in a suitable oil or 0.1 to 5.0% w/v as the pure crystalline compound, 2–20% of an emulsifier having an HLB (hydrophilic/lipophilic balance) value of between 10 and 18 or where a blend of emulsifiers is employed, a calculated HLB value of between 10 and 18 and 0.1 to 1.0% of an antioxidant or a mixture of antioxidants. Processes for preparation of the compositions and their use in the preparation of beverages are provided.

9 Claims, No Drawings

COMPOSITIONS

The present invention relates to liquid compositions comprising of oil-soluble ingredients for use in the maintenance and/or promotion of health. In particular the invention relates to compositions for colouring products for internal or external use by humans or animals, such as beverages, processes for preparing such compositions and products containing them.

Brightly coloured food and drink products have considerable consumer appeal. In the case of beverages of the 'health' or 'energy' type, a clear product is also highly desirable for the product as it enhances the 'clean and fresh' image of such products. A clear product also has benefits in terms of assisting the detection of spoilage by certain microorganisms.

To produce clear and brightly coloured yellow/orange/red beverages it is known to use any one of a number of synthetic dyes which are permitted for food use such as Tartrazine, Sunset Yellow FCF and Carmoisine. The 'azo' colourants are particularly useful in largely water-based beverages in view of their solubility in water and stability to light. These chemical and physical characteristics have allowed the production of many commercially successful products containing these colourants as principal colouring ingredients.

A major disadvantage of using these azo-colourants is the fact that they are artificial products as opposed to-naturally occurring products. Because of the increasing consumer awareness of the use of artificial additives in food and media interest in food products there is increasing pressure on manufacturers to offer consumers the choice of products coloured with permitted, non-azo food colours with a particular preference for 'naturally-occurring' colours. Unfortunately, the colouring of transparent, water-based products with many non-azo colours is extremely difficult because the majority of the available yellow and or orange colourants are oil soluble.

Carotenoids are naturally-occurring yellow to red pigments of the terpenoid group which can be found in plants, algae and bacteria. They include 'carotene' (a mixture of α and β-carotenes but mostly β-carotene),α-carotene, β-carotene, γ-carotene, lycopene, zeaxanthin, lutein (a xanthophyll), bixin (eg. from solvent extracted annatto), capsanthin (paprika), canthaxanthin, astaxanthin, actinioerythrol, violerythrin, β-8'-apo-carotenal (apo-carotenal), β-12'-apo-carotenal and esters of hydroxyl- or carboxyl-containing members thereof. Many of the naturally occurring colourants can be made synthetically, for example much of the β-carotene used commercially has been made synthetically. Many of the carotenoids occur in nature as cis and trans-isomeric forms, while synthetic compounds are frequently racemic mixtures.

Carotenoids have been of interest as a source of added colour for food and drink products. However, their insolubility in water and poor solubility in the conventional oils used in food products and their sensitivity to oxidation has limited their use, particularly in water-based products such as beverages and syrups and products to which water is to be added.

UK patent specification 1 407 779 (Hoffman-La Roche) describes a carotenoid colouring composition which is dispersible in water to form optically clear aqueous dispersions. These known compositions essentially contain large amounts of the emulsifiers polysorbate 60 and 80 along with a particular mixture of low molecular weight saturated coconut fatty acids and saturated fractions of coconut oil triglycerides. However it is generally undesirable to have large amounts of these emulsifiers present. In particular polysorbate 80 has undesirable taste characteristics such that if used in the amounts specified the predominantly 'oily' or 'fatty' taste would be inappropriate for most beverages. Also the amounts required would add significantly to the cost. We have now developed a composition which does not rely on large amounts of fatty acids, triglycerides and emulsifiers to create a stable formulation.

The present invention therefore provides an aqueous composition for the preparation of optically clear products for human or animal healthcare comprising 0.1 to 2.0% w/w of an oil-soluble ingredient as a 20–30% w/w dispersion in a suitable oil or 0.1 to 5.0% w/v as the pure crystalline ingredient ,2–20% of an emulsifier having an HLB (hydrophilic/lipophilic balance) value of between 10 and 18 or where a blend of emulsifiers is employed, a calculated HLB value of between 10 and 18 and 0.1 to 1.0% of an antioxidant or a mixture of antioxidants. An example of a blend of emulsifiers is a blend containing 4 parts of Span 20 (sorbitan monolaurate) and 6 parts of Tween 60 (polyoxyethylene sorbitan monostearate) having an effective HLB value of 0.4×8.6+0.6×14.9=12.3.

By 'optically clear' we mean a product exhibiting a percentage transmittance value of not less than about 95%, preferably 98%, determined at a wavelength of 800 nm in a 1 cm path length cuvette. Preferably the composition is a colour composition wherein the oil-soluble ingredient comprises a colouring agent and/or an antioxidant or a mixture of antioxidants.

Surprisingly it has been found that the composition of the present invention is able to yield a product with desirable properties, particularly high water solubility using ingredients which have hitherto been found to be difficult to solubilise satisfactorily in this kind of product.

Preferably the oil-soluble colouring ingredient is a carotenoid. Preferably the carotenoid is β-carotene or apocarotenal. Suitably the mount of carotenoid is 0.1–2.0%, preferably 0.1–1.0% by weight expressed as the pure substance. Carotenoids for use in the present invention can be extracted from natural sources by processes known in the art, see for example: Stevens, B. (1988), Food Production, p34, and Emmam, S. S., Ibrahim, S. S., Ahsous, M. M. S., Askar, A. (1991), Fluss. Obst., 57(5), 287–288; 295–297. The carotenes and apo-carotenal are also readily available as synthetic nature-identical colours [Emodi, A. (1978), Food Tech. 32(5), 32–42, 79.] Carotenoids are commercially available in pure form from Sigma Chemical Co., Poole, Dorset or as dispersions in vegetable oil from Roche Products Ltd., Welwyn Garden City, Herts. Carotenoids eg carotenes are known to exist in more than one isomeric form and the present invention can be applied to and encompasses the use of all the various isomeric forms.

Mixtures of colours can also be used in the composition according to the invention, in particular β-carotene with apocarotenal to produce an attractive orange colour. A dispersion of β-carotene according to the invention can also be used in admixture with other colouring materials to reproduce a range of different hues. When mixed with sodium copper chlorophyllin, a wide range of time yellow shades can be reproduced; with carminic acid, carmine, or anthocyanin extracts an extensive range of orange shades can be prepared.

Suitable oils according to the present invention include, in particular, consumable oils for example, corn, peanut, safflower, olive and rapeseed oils as well as many essential oils particularly those used in beverages used to give flavours, such as citrus oils.

The emulsifier may be any anionic, cationic, amphoteric or non-ionic emulsifier or mixture of emulsifiers which is suitable for consumption by or application to the human or animal body. Preferably the emulsifier is a non-ionic emulsifier or a mixture and preferably having an HLB (hydrophilic/lipophilic balance) of 12–16 and most preferably has an HLB value of 15. Preferred compounds include Tween 60 (polyoxyethylene(20)sorbitan monostearate and Tween 40 (polyoxyethylene(20)sorbitan monopalmitate) available from ICI Speciality Chemicals, Leatherhead, Surrey.

Suitably the emulsifier is a binary or tertiary blend of emulsifiers, for example blends of Tween 60 with a sucrose ester emulsifier (manufactured by Mitsubishi Kasei Food Corporation, Ichikawa Building, 13-3 Ginza 5-Chome, Chuo-ku, Tokyo 104, Japan) or blends of Tween 60 and sucrose ester and a polyglycerol ester of a fatty acid (available from Grindsted Products Limited., Northern Way, Bury St. Edmunds, Suffolk).

The amount of emulsifier in the composition is selected as an amount which will vary depending upon which specific oil-soluble ingredient is used, its method of preparation, and how much is included. For example a dispersion of β-carotene in oil will require a higher concentration of emulsifier or blend of emulsifiers to disperse the oil and the carotenoid than the corresponding quantity of crystalline compound. For example an oil-based dispersion containing 30% by weight of pigment will generally require emulsifier(s) in the range of 8–10% w/w to achieve a clear dispersion and so as not to have significant adverse flavour effects in typical drinks when diluted. In contrast only 2–5% of emulsifier(s) will generally be needed if the equivalent concentration of pure compound is employed.

Preferably the emulsifier is a polysorbate, in particular polysorbate 60 in the case of consumable products as it has the advantage of having the least noticeable taste. Therefore, a particularly useful feature of the present invention is the ability to produce a flavourless colour composition. In a particularly preferred composition the carotenoids are apocarotenal and β-carotene and the emulsifier is a polysorbate.

The antioxidant used in the present invention can be for example, alphatocopherol, ascorbic acid, ascorbyl palmitate, butylated hydroxyanisole (BHA) and butylated hydroxytoluene (BHT) or a mixture of such antioxidants. Particularly preferred antioxidants are α-tocopherol, ascorbyl palmitate and ascorbic acid.

An important advantage of the compositions of the present invention over known compositions is one of economy since it avoids the use of large amounts of added lipids and emulsifiers. The compositions are simpler than those already known for the incorporation of carotenoids into drinks and can be used to give a wider range of products, particularly reduced fat products with new and interesting flavour possibilities. A further advantage of the present invention is that the composition can be combined with a wide range of natural and artificial colours to yield an extended range of hues in aqueous products.

Whilst the present invention is particularly useful in the production of optically clear products, the present invention can also be used to prepare opaque, cloudy products. A frequent problem with such products, particularly those products containing emulsified carotenoids is that of 'neck ringing'. The compositions prepared according to the present invention have been found not to exhibit this problem. It will be appreciated that the compositions of the present invention may be used to colour liquid consumable products in the pharmaceutical or veterinary field other than beverages, such as vitamin and cough syrups, throat sprays, lotions and mouthwashes, particularly where optical clarity is important.

Certain carotenoids can act as vitamins and provitamins. In the compositions of the present invention the carotenoids and other oil-soluble components are believed to be finely dispersed in a micellar form or as microemulsions because they exhibit certain characteristics eg. transparency when viewed by transmitted light.

Therefore a further advantage of the compositions according to the present invention is that the fine dispersion of these oil-soluble vitamins, pro-vitamins and other oil-soluble materials in aqueous preparations will help to promote the efficient uptake of such materials by body tissues when the composition is presented to the body. Whilst the small particle size of the particles of oil-soluble ingredients favour uptake of the oil-soluble materials, the simultaneous presentation or ingestion of oil-soluble active compounds with an emulsifier will also encourage efficient transfer of these substances across membranes.

The formulations according to the invention also have surprising acid resistance. This is advantageous because prior to absorption from the intestinal tract, the preparation is able to survive the strongly acid conditions of the stomach.

In a further aspect of the invention there is provided a method of administration of an oil-soluble material to human or animal body by treating said body with a composition according to the invention. Preferably the composition is administered orally, for example in the form of a liquid composition.

The composition obtained according to the present invention is an aqueous dispersion which is capable of dissolution in water-based products to yield optically clear finished products.

It will be appreciated that further ingredients may optionally be included in the composition of the present invention or to the final food product, for example sweeteners, preservatives (eg. sulphur dioxide, benzoic acid and sorbic acid), proteins, fats, vitamins, minerals and other materials employed in the preparation of food and drink products. Optionally the compositions also contain antioxidant cofactors such as zinc, selenium and manganese which are needed for the body's naturally occurring antioxidant enzymes. Preferably the final product is flavoured; this can be achieved by the addition of naturally flavoured foods such as fruit juices and concentrates, extracts and compounds or flavouring additives. Preferably further nutritive ingredients are added to the final drink such as other vitamins and minerals as described in "The Food Labelling Regulations 1984" Statutory Instrument No. 1305 (1984) H. M. S. O., London.

Suitably processing aids can be incorporated. Such aids may include ingredients which influence pH, redox potential, enzyme activity, hydrogen bonding and/or other aspects. Processing aids are for example sulphur dioxide, other antioxidants, metal salts, acids (eg. phosphoric and citric acid), alkalis, surfactants such as lecithin and starch plasticisers eg. calcium chloride. Preferred processing aids for inclusion are anti-foaming agents eg. silicones.

Ingredients subject to a loss of nutritional value are added at a late stage of the process. Optionally the product can be produced in light or oxygen excluding containers after preparation to increase protection of materials sensitive to light or oxygen induced degradation. Optionally the product can be carbonated.

U.S. Pat. No. 4,435,427 [BASF] discloses a process for preparing micellar solutions of β-carotene which involves heating the β-carotene and a non-ionic emulsifier at from 160°–180° C. and cooling the hot homogeneous mixture by adding water to the mixture.

A further aspect of the invention provides a process for the preparation of an aqueous composition for the preparation of optically clear products for use in human or animal healthcare which process comprises:

a) dispersing the antioxidant in the emulsifier(s) while heating to a temperature of approximately 40° C.

b) dispersing one or more oil-soluble ingredients in the mixture in a) above while heating to between about 80+–200° C. so as to yield a transparent mixture, c) adding optionally a further oil-soluble ingredient, d) raising the temperature of the mixture as appropriate whilst maintaining stirring to maintain a transparent mixture and e) combining the mixture with water having a minimum temperature of 95° C. while continuously stirring to provide a transparent composition. Preferably the mixture and the water are combined by adding the mixture to the water.

One advantage of the present invention is the wide range of temperatures which can be used in b) above. The temperature developed in mixing in b) is preferably 80°–160° or 180°–200° C. The lower temperatures are particularly useful where more temperature sensitive ingredients are involved. The higher temperatures are useful in that significantly less emulsifier(s) is needed. In particular it has been found that when pure β-carotene has been used as the oil-soluble ingredient, an increase in temperature permits a reduction in the amount of emulsifier(s) required to achieve optical clarity. Therefore to minimise the amount of emulsifier(s) used, a temperature of not less than 160° C. or preferably 180° C. is preferred. The use of these high temperatures incurs the risk of degradation of pigment unless suitable precautions are taken. For example it is necessary to incorporate an antioxidant in the initial stages of preparation and it is desirable to exclude oxygen by heating the mixture in an atmosphere of nitrogen.

In the preparation of the composition according to e) above it is important that the mixture is combined with the water gradually so as to maintain transparency and for best or most consistent results the mixture is added to the water.

In a preferred process, crystalline β-carotene is dissolved in polysorbate emulsifier which contains a suitable antioxidant, preferably α-tocopherol. In another preferred process according to the present invention an oily suspension of apo-catorenal is added to a polysorbate emulsifier/antioxidant mixture. The primary addition of the apo-carotenal has the advantage of promoting the dissolution of carotene which is subsequently added in the form of a suspension in oil. It is also advantageous to include apocarotenal as it helps to stabilise β-carotene.

In a further aspect of the present invention additional water is added to the composition to yield an aqueous intermediate product which is suitable for use in a suitable water-based product.

The invention is illustrated by the following Examples.

EXAMPLE 1—Colour Composition

|  | % w/w |
| --- | --- |
| β-carotene (crystalline) | 1.0 |
| antioxidant (α-tocopherol) | 0.3 |
| emulsifier (Polysorbate 40 or 60) | 7.5 |
| water to | 100 |

The above components are combined as follows. The antioxidant is dispersed in the emulsifier while heating to approximately 40° C. The β-carotene is then added and the temperature of the mixture raised to at least 140° C. while maintaining stirring. At this point the mixture should be transparent. The mixture is added slowly at a rate of 50 ml per minute to about 75% of the final volume of hot water having a minimum temperature of 95° C. while maintaining stirring. The diluted mixture is cooled to room temperature and diluted with water to the final volume. As an alternative after adding the β-carotene and heating as given above the hot water is added slowly to the β-carotene mixture at the rate of 50 ml per minute while stirring. When half the volume of water has been added there is a noticeable increase in viscosity. Continuing to add the water to the required volume reduces the viscosity and yields a clear, orange-black composition.

EXAMPLE 2—Colour Composition

|  | % w/w |
| --- | --- |
| β-carotene (30% dispersion) | 0.33 |
| apo-carotenal (20% dispersion) | 1.5 |
| antioxidant (α-tocopherol) | 0.3 |
| emulsifier (Polysorbate 40 or 60) | 9 |
| water to | 100 |

The antioxidant is dispersed in the emulsifier while heating to approximately 40° C. The apo-carotenal is added while heating to approximately 80° C. and stirred to yield a transparent mixture. The β-carotene is then added while continuing to stir and the temperature of the mixture raised to 140° C. At this point the mixture should remain transparent. Finally, the mixture is added to hot water as detailed in Example 1 above.

EXAMPLE 3—Colour Composition

|  | % w/w |
| --- | --- |
| β-carotene (crystalline) | 1.0 |
| antioxidant (α-tocopherol) | 0.3 |
| emulsifier 1 (Polysorbate 60) | 6.0 |
| emulsifier 2 (sugar ester S-1170) | 0.25 |
| emulsifier 3 (Triodan) | 0.25 |
| water to | 100 |

The antioxidant is dispersed in emulsifier 1 while heating to approximately 40° C. Emulsifiers 2 and 3 are added and the temperature raised to 140° C. The β-carotene is added while maintaining stirring; at this point the mixture should be transparent. Finally, the mixture is added to hot water as detailed in Example 2.

EXAMPLE 4—Colour Stability Data

The colour stability of the compositions according to the present invention were determined using the following simulated shelf and accelerated storage tests.

4.1 Stabilising Effect of Ascorbic Acid and apo-carotenal

Incorporation of ascorbic acid in the final product is effective in reinforcing the stabilising effect of the antioxidants. This is illustrated with data from a study in which combinations of β-carotene, apo-carotenal and ascorbic acid were incorporated in a typical beverage formulation. The products were stored in bright daylight conditions for a period of 30 days and the colour loss at the end of this period was determined by spectrophotometry.

| β-carotene mg/L | apo-carotenal mg/L | ascorbic acid mg/L | % of original colour |
|---|---|---|---|
| 2 | 1 | 100 | 49 |
| 2 | 1 | 300 | 80 |
| 4 | 2 | 0 | 0 |
| 4 | 2 | 200 | 80 |
| 4 | 2 | 400 | 89 |
| 6 | 1 | 100 | 37 |
| 6 | 1 | 300 | 83 |
| 6 | 3 | 100 | 70 |
| 6 | 3 | 300 | 93 |

4.2 Stabilising Effect of α-tocopherol

Test beverages were prepared using the colour composition described in Example 2 to provide 1–3 mg of carotenoids in a ready-to-drink product. Similar beverages but without the anti-oxidant (α-tocopherol) were also prepared. The products were packaged in conventional sealed glass bottles and tested in a high intensity light and heat exposure unit for a period of 240 hours and samples were analysed at intervals for colour retention. At the end of this period, the samples containing the antioxidant exhibited a greater retention of colour than products coloured similarly but without the addition of the antioxidant (see below)

| | % of original colour | |
|---|---|---|
| Time (hours) | variant 1 | variant 2 |
| 0 | (100) | (100) |
| 48 | 64 | 69 |
| 98 | 39 | 57 |
| 146 | 18 | 35 |
| 194 | 19 | 34 |
| 242 | 8 | 18 | variant 1 - without antioxidant
variant 2 - with antioxidant

Bottles were also placed on a shelf storage position exposed to north-eastern daylight at ambient temperatures for up to 12 months. Samples were analysed at monthly intervals for colour retention by measuring their absorbance values at 460 nm and expressing this as a percentage of the original colour. As can be seen from the results below the samples containing the antioxidant exhibited a greater retention of colour than products coloured similarly but without the addition of antioxidant.

| | % of original colour | |
|---|---|---|
| Time (months) | Variant 1 | Variant 2 |
| 0 | 100 | 100 |
| 1 | 93 | 95 |
| 2 | 76 | 85 |
| 3 | 66 | 73 |
| 6 | 39 | 50 |
| 12 | 25 | 36 |

VARIANT 1: Without antioxidant
VARIANT 2: With antioxidant

4.3 Stability of β-carotene—Carminic Acid Combination

Test products were prepared using 1.125 mg β-carotene and 2.7 mg carminic acid and tested as detailed in section 4.2 for a period of 380 hours. The samples exhibited satisfactory stability of colour under these extreme conditions.

| Time (hours) | % of original colour |
|---|---|
| 0 | (100) |
| 24 | 94 |
| 72 | 94 |
| 96 | 92 |
| 144 | 89 |
| 192 | 83 |
| 240 | 82 |
| 288 | 83 |
| 384 | 76 |

4.4 Stability of β-carotene—Carmine Combination

Acid-stable carmine can be substituted for carminic acid with similar results to those exhibited with carminic acid. The test product contained 1.125 mg β-carotene and 0.75 mg carmine and was tested as detailed in section 4.2.

| Time (hours) | % of original colour |
|---|---|
| 0 | 100 |
| 24 | 98 |
| 67 | 96 |
| 178 | 90 |
| 225 | 82 |
| 294 | 82 |
| 462 | 78 |

EXAMPLE 5—Formulations

5.1 Carbonated, clear citrus flavoured drink

| | % w/v |
|---|---|
| Sucrose | 10.0 |
| Citric acid | 0.25 |
| Sodium benzoate | 0.017 |
| Ascorbic acid | 0.030 |
| Flavouring as required | |
| Colour composition 1 | 0.2 (% v/v) |
| Water | to 100 vol |
| Carbon dioxide to 2.5 volumes | |

Using a β-carotene of the type detailed in example 1, experimental products have been prepared containing the carotenoid in concentrations ranging from 2.5 to 400 mg per litre. They ranged in colour from pale lemon yellow to an intense orange and all were characterized by possessing optical clarity without any evidence of 'neck ringing'.

Typical opaque drink products in which the colour compositions can be employed are (examples 5.3 and 5.3):

5.2 Carbonated fruit crush drink

| | % w/v |
|---|---|
| Orange juice | 5.2 |
| Sucrose | 7.5 |
| Citric acid | 0.3 |
| Sodium benzoate | 0.007 |

5.2 Carbonated fruit crush drink

| | % w/v |
|---|---|
| Ascorbic acid | 0.040 |
| Colour composition 2 | 0.2 (% v/v) |
| Flavouring as required | |
| Water | to 100 vol |
| Carbon dioxide to 2.5 volumes | |

5.3 Citrus flavour milk drink

| | % w/v |
|---|---|
| Skimmed milk | 51.0 |
| Carbohydrate | 9.4 |
| Citric acid | 0.9 |
| Sodium carboxymethylcellulose | 0.94 |
| Ascorbic acid | 0.030 |
| Colour composition 3 | 0.3 (% v/v) |
| Flavourings as required | |
| Water | to 100 vol |

5.4 Cough Syrup

| | % w/v |
|---|---|
| Dextromethorphan HCl | 0.15 |
| Glucose syrup | 60.0 |
| Glycerine | 10.0 |
| Propylene glycol | 9.0 |
| Sodium benzoate | 0.1 |
| Sodium citrate | 0.024 |
| Citric acid monohydrate | 0.28 |
| Saccharin sodium | 0.1 |
| Flavouring as required | |
| Colour composition 1 | 0.2 (% v/v) |
| Water | to 100 vol |

5.5 Sore throat spray

| | % w/v |
|---|---|
| Hexylresorcinol | 0.08 |
| Alcohol (96%) | 15.0 (% v/v) |
| Menthol | 0.04 |
| Glycerol | 35.0 |
| Sodium citrate | 0.04 |
| Citric acid | 0.05 |
| Sodium lauryl sulphate | 0.05 |
| Flavouring as required | |
| Colour composition 1 | 2.0 (% v/v) |
| Water | to 100 vol |

5.6 Antioxidant vitamin syrup

| | % w/v |
|---|---|
| Tocopherol acetate | 0.633 |
| Ascorbic acid | 1.333 |
| Glucose syrup | 85.0 |
| Propylene glycol | 1.0 |
| Sodium citrate | 0.024 |
| Citric acid | 0.25 |
| Sodium benzoate | 0.1 |
| Flavourings as required | |
| Colour composition 1 | 10.0 (% v/v) |
| Water | to 100 vol |

5.7 Mouthwash

| | % w/v |
|---|---|
| Ethanol | 15.0 |
| Cetylpyridinium chloride | 0.05 |
| Sodium fluoride | 0.05 |
| Saccharin sodium | 0.05 |
| Flavourings as required | |
| Colour composition 1 | 0.2 (% v/v) |
| Water | to 100 vol |

5.8 Suntan Lotion

| | % w/w |
|---|---|
| Octyl methoxy cinnamate | 5.5 |
| Butyl methoxydibenzoyl methane | 1.0 |
| Tocopherol acetate | 0.5 |
| Stearic acid | 1.8 |
| Glyceryl stearate | 2.25 |
| White mineral oil | 10.0 |
| Glycerine | 5.0 |
| Dimethicone | 0.5 |
| Carbomer | 0.1 |
| Triethanolamine | 0.52 |
| Perfume as required | |
| Colour composition 1 | 0.2 (% v/v) |
| Water | to 100% w/w |

EXAMPLE 6—Experiments with Crystalline β-carotene

Experiments were carried out to determine the effect of increasing temperature on the amount of emulsifier(s) required to achieve optical clarity. 1 g of crystalline β-carotene required the following amounts of Tween 60 at the temperatures stated

| Temp (°C.) | Tween 60 (g) |
|---|---|
| 140 | 10.5 |
| 160 | 7.5 |
| 180 | 4.0 |
| 200 | 3.0 |

EXAMPLE 7—Resistance to Acid Digestion

The following is a simulation the acid conditions of the stomach to assess the performance of preparations containing β-carotene derived from a clear 'micellar' solution (Example 1 above) or equivalent amounts of β-carotene dispersed as a conventional emulsion using commercially available preparations of β-carotene as a 5% liquid emulsion (beverage no 2) or as beadlets containing β-carotene (beverage no 3).

Test drinks were prepared containing 30 mg β-carotene per litre and 1 volume of each product was mixed with 4 volumes of 1M hydrochloric acid. The acidified drinks were placed in a shaking water-bath maintained at 37° C. After 1 hour, solutions were removed and examined visually and by optical microscopy. The following observations were recorded:

| Test Drink | Visual Assessment | Microscopy |
|---|---|---|
| 1 (Clear beverage) Example 1 | Optical clarity maintained No loss of colour No "ringing" | No evidence of oil droplet formation or breakdown of micelles |
| 2 (opaque beverage) | Breakdown of emulsion Loss of colour Deposition of β-carotene on surface | Extensive aggregation of β-carotene crystals Interstitial oil droplets present throughout field |
| 3 (opaque beverage) | No loss of colour or apparent loss of colour | Some evidence of crystal formation and aggregation but not as extensive as in drink 2 |

EXAMPLE 8 Particle Size

In order to make some assessment of the size of the "particles" present in the test products detailed above, aliquots of the three drinks were passed through membrane filters of known porosities. The membranes employed were Whatman Type WCN of pore sizes 5 μm and 0.65 μm respectively. In the case of the transparent product the loss of colour was determined by spectrophotometry of the drink pre- and post-filtration. This technique was unsuitable for the opaque products and a visual assessment was made of the filtrates.

| Test Drink | % of Original Colour 5 μm | % of Original Colour 0.65 μm |
|---|---|---|
| 1 (clear beverage) | 100 | 96 |
| 2 (opaque beverage) | 5 | 1 |
| 3 (opaque beverage) | 50 | 20–25 |

Therefore it can be concluded that the formulations according to the invention have micelles or similar particles of a size not greater than about 0.65 μm.

EXAMPLE 9—Bioavailability Studies—Protocol for Human Volunteer Study

The extent of bioavailability of a formulation according to the invention can be demonstrated by measuring the appearance of β-carotene in blood serum following the daily ingestion of 15 mg doses either in the form of a clear formulated drink according to the invention or as β-carotene capsules (Roche 'REDOXON'). The initial uptake and amplitude of response is measured to measure the extent of the bioavailability for each dosage form.

20 subjects, male and female age 18–50 years are used but volunteers with any history or biochemical evidence of liver, kidney or pancreatic disease, anaemia, hyperlipidaemia or maladsorption syndromes are excluded. Subjects taking vitamin, β-carotene or other supplements and medications suspected of interfering with the absorption of fat-soluble actives are excluded as are those individuals on a vegetarian diet, those not following normal dietary practices, subjects with weights greater or less than 20% of the ideal for their height, age and sex, smokers, pregnant females, females taking oral contraceptives and those whose diet contains greater than an estimated intake of 3.5 mg β-carotene per day.

Diet—Dietary fat and β-carotene intakes of the subjects are established by questionnaire. Subjects have a free choice of diet during the study except for the diet prior to dosing. The prescribed breakfast is a choice of non-maize based cereal with a skimmed or semi-skimmed milk, yoghourt (plain or red fruit), coffee or tea with skimmed or semi-skimmed milk, non-carotenoid containing fruit juice or conserves. Fat intake is avoided. At other times a normal diet is followed but with the exclusion of incidences of high fat intake eg. cream, and foods containing high concentrations of β-carotene.

Test materials—Beverage formulated according to the invention with permitted food ingredients to contain 15 mg β-carotene per 250 ml. 15 minutes are allowed for consumption of drink or Roche Products REDOXON capsules containing 15 mg β-carotene; capsules are swallowed with 250 ml water.

| Experimental design: | |
|---|---|
| Time (h) | |
| −48 | blood sample |
| −1 | breakfast |
| 0 | blood sample followed by dose 1 |
| +2 | blood sample |
| +4 | blood sample |
| +8 | blood sample |
| +23 | breakfast |
| +24 | blood sample followed by dose 2 |
| +47 | breakfast |
| +48 | blood sample followed by dose 3 |
| +71 | breakfast |
| +72 | blood sample followed by dose 4 |
| +95 | breakfast |
| +96 | blood sample followed by dose 5 |
| +119 | breakfast |
| +120 | blood sample followed by dose 6 |
| +143 | breakfast |
| +144 | blood sample followed by dose 7 |
| +168 | blood sample |

4 weeks after completion of this leg, the design is repeated for each subject with the second test material. The order in which the regimens are undertaken are varied for each subject.

Sampling and Analysis:

10 ml samples of blood are collected by means of an indwelling catheter inserted in a forearm vein on day 1 of the regimen; thereafter, samples are withdrawn by means of a syringe. Following separation of the serum, the serum samples are stored at −24° C. for later analysis by HPLC.

We claim:

1. A process for preparing a stable aqueous composition for the preparation of optically clear products for use in human or animal healthcare, said process comprising:

a) dispersing 0.1–1.0% (w/w based on the product of step e) of an antioxidant in 2–20% (w/w based on the product of step e) of an emulsifier or mixture of emulsifiers having an HLB (hydrophilic/lipophilic balance) value of between 10–18 while heating to a temperature of approximately 40° C.;

b) dispersing 0.1 to 5.0% (w/w based on the product of step e) of one or more oil-soluble ingredients or 0.1–2.0% (w/w based on the product of step e) of one or more oil-soluble ingredients as a 20–30% (w/w based on the dispersion) dispersion in a suitable oil in the mixture in a) above while heating to between about 80°–200° C. so as to yield a transparent mixture, c) adding optionally a further oil-soluble ingredient;

d) raising the temperature of the mixture as appropriate whilst maintaining stirring to maintain a transparent mixture, and e) combining the mixture with water having a minimum temperature of 95° C. while continuously stirring to provide a transparent composition.

2. A process according to claim 1 wherein in e) the mixture is added to the water.

3. An aqueous composition for the preparation of optically clear products for use in human or animal healthcare wherein said composition is made by the process of claim 1.

4. A composition as claimed in claim 3 wherein the oil-soluble ingredient is a colouring ingredient and/or an antioxidant or mixtures thereof.

5. A composition as claimed in claim 4 wherein the colouring ingredient is a one or more carotenoids which is β-carotene or a mixture of β-carotene and apo-carotenal.

6. A composition as claimed in claim 4 wherein the mount of carotenoid is 0.1–1.0 % w/w.

7. A composition as claimed in any one of claim 3 wherein the mount of emulsifier is between 8 and 10% w/w.

8. A composition as claimed in any one of claim 3 wherein the amount of antioxidant is 0.3–0.5 % w/w.

9. A composition according to any one of claim 3 in which ascorbic acid or alpha-tocopherol or both are present.

* * * * *